United States Patent
Ahiska

(10) Patent No.: US 9,522,205 B2
(45) Date of Patent: Dec. 20, 2016

(54) MULTI MODE LOW TEMPERATURE PLASMA STERILIZER

(71) Applicant: GOA TEKNOLOJI DANISMANLIK ELEKTRONIK, IMALAT TICARET ITHALAT IHRACAT A.S., Ankara (TR)

(72) Inventor: Fatih Ahiska, Ankara (TR)

(73) Assignee: GETINGE STERICOOL MEKICAL ALTETLER SAN. VE TIC. A.S., Sincan, Ankara (TR)

( * ) Notice: Subject to any disclaimer, the term of this patent is extended or adjusted under 35 U.S.C. 154(b) by 252 days.

(21) Appl. No.: 13/956,842

(22) Filed: Aug. 1, 2013

(65) Prior Publication Data
US 2014/0037495 A1 Feb. 6, 2014

Related U.S. Application Data

(60) Provisional application No. 61/678,657, filed on Aug. 2, 2012.

(51) Int. Cl.
*A61L 2/24* (2006.01)
*A61L 2/14* (2006.01)
*A61L 2/20* (2006.01)

(52) U.S. Cl.
CPC .. *A61L 2/24* (2013.01); *A61L 2/14* (2013.01); *A61L 2/208* (2013.01); *A61L 2202/24* (2013.01)

(58) Field of Classification Search
CPC ............... A61L 2/208; A61L 2/24; A61L 2/14
See application file for complete search history.

(56) References Cited

U.S. PATENT DOCUMENTS

| 4,169,123 A | 9/1979 | Moore et al. |
| 4,169,124 A | 9/1979 | Forstrom et al. |
| 4,642,165 A | 2/1987 | Bier |
| 4,643,876 A | 2/1987 | Jacobs et al. |
| 4,744,951 A | 5/1988 | Cummings et al. |
| 4,756,882 A | 7/1988 | Jacobs et al. |

(Continued)

FOREIGN PATENT DOCUMENTS

WO 2005/067984 A1 7/2005

OTHER PUBLICATIONS

Beatriz Unger-¬ -Bimczok, Volker Kottke, Christian Hertel, Johannes Rauschnabel, "The Influence of Humidity, Hydrogen Peroxide Concentration, and Condensation on the Inactivation of Geobacillus Stearothermophilus Spores with Hydrogen Peroxide Vapor", Journal of Pharmaceutical Innovation, vol. 3, No. 2 (Jun. 28, 2008), pp. 123-133.

(Continued)

*Primary Examiner* — Regina M Yoo
(74) *Attorney, Agent, or Firm* — Thomas | Horstemeyer, LLP

(57) ABSTRACT

In a low temperature hydrogen peroxide gas plasma sterilizer, the accurate control of concentration of the hydrogen peroxide sterilant is an important factor in determining reliability and sterilization efficacy of the sterilization process. The present application describes sterilizers, and sterilization methods, which use a novel injector-concentrator arrangement which allows accurate concentration of the sterilant performed concurrently with the sterilization process. This process enables the device to sterilize wide range of sensitive equipment within a shorter sterilization cycle.

6 Claims, 7 Drawing Sheets

(56) References Cited

U.S. PATENT DOCUMENTS

| | | | |
|---|---|---|---|
| 4,956,145 A | 9/1990 | Cummings et al. | |
| 8,192,685 B2* | 6/2012 | Lukasik | 422/67 |
| 2010/0108580 A1* | 5/2010 | Lukasik | 209/659 |
| 2013/0024134 A1* | 1/2013 | Lukasik | 702/29 |
| 2013/0074612 A1* | 3/2013 | Lukasik | 73/863.23 |
| 2013/0302207 A1* | 11/2013 | Ahiska | 422/3 |

OTHER PUBLICATIONS

James R. Rickloff "Factors Influencing Hydrogen Peroxide Gas Sterilant Efficacy", Advanced Barrier Inc. Nov. 12, 2008.

Sterrad NX Sterilization System—User's Guide (Ref 99920), Advanced Sterilization Products—a Johnson & Johnson Company, Division of Ethicon, Inc., Sep. 2008.

Sterrad 100NX Sterilizer System—User's Guide (Ref 99970), Advanced Sterilization Products—a Johnson & Johnson Company, Division of Ethicon, Inc., Feb. 2008.

Sterrad 100 Sterilization System Service Guide, Advanced Sterilization Products Services, Inc., 1997.

Jacobs, Paul T., Sterrad 100S Sterilization System, Advanced Sterilization Products—a Johnson & Johnson Company, Division of Ethicon, Inc., 1999.

Sterrad 100NX Sterilization System—Service Troubleshooting Guide, Advanced Sterilization Products—a Johnson & Johnson Company, Division of Ethicon, Inc., Jun. 2007.

Sterrad 100NX—Expand Your Flexible Endoscope Processing Capabilities—Introducing the Sterrad 100NX System Duo Cycle—a Johnson & Johnson Company, Division of Medos International Sarl, 2011.

* cited by examiner

MULTI MODE LOW TEMPERATURE PLASMA STERILIZER

BACKGROUND

The present application relates generally to sterilization of objects, and more particularly to sterilization of medical apparatus using both hydrogen peroxide vapor and a glow discharge.

Note that the points discussed below may reflect the hindsight gained from the disclosed inventions, and are not necessarily admitted to be prior art.

Some background information can be found in the following documents, all of which are hereby incorporated by reference: Beatriz Unger-Bimczok, Volker Kottke, Christian Hertel, Johannes Rauschnabel, "The Influence of Humidity, Hydrogen Peroxide Concentration, and Condensation on the Inactivation of Geobacillus stearothermophilus Spores with Hydrogen Peroxide Vapor", Journal of Pharmaceutical Innovation, Vol. 3, No. 2 (28 Jun. 2008), pp. 123-133; James R. Rickloff "Factors Influencing Hydrogen Peroxide Gas Sterilant Efficacy", Advanced Barrier Inc. Nov. 12, 2008; U.S. Pat. Nos. 4,169,123, 4,169,124, 4,643,876, 4,756,882, 4,956,145, 4,642,165, and 4,744,951; PCT application WO 2005/067984; the Sterrad NX Sterilizer user and service manuals (from Advance Sterilization Products); and the Sterrad 100S Sterilizer user manual and service manuals.

Medical instruments were traditionally sterilized either with heat, such as is provided by steam, or a chemical, such as formaldehyde or ethylene oxide in the gas or vapor state. Each of these methods has drawbacks. Many medical devices, such as fiberoptic devices, endoscopes, power tools, etc. are sensitive to heat, moisture, or both. Formaldehyde and ethylene oxide are both toxic gases that pose a potential hazard to healthcare workers. Problems with ethylene oxide are particularly severe, because its use requires long aeration times to remove the gas from articles that have been sterilized. This makes the sterilization cycle time undesirably long.

Sterilization using liquid hydrogen peroxide solution has been found to require high concentration of sterilant, extended exposure time and/or elevated temperatures. However, sterilization using hydrogen peroxide vapor has been shown to have some advantages over other chemical sterilization processes (see, e.g., the '123 and '124 documents cited above).

The combination of hydrogen peroxide with a plasma provides certain additional advantages, as disclosed in the '876 document cited above. The '882 document cited above discloses the use of hydrogen peroxide vapor, generated from an aqueous solution of hydrogen peroxide, as a precursor of the reactive species generated by a plasma generator. The combination of hydrogen peroxide vapor diffusing into close proximity with the article to be sterilized and plasma acts to sterilize the articles, even within closed packages.

However, these methods of combining hydrogen peroxide vapor with a plasma, while useful in "open" systems, have been found to be inadequate to effect sterilization in articles having diffusion-restricted areas, since the methods are dependent upon diffusion of the sterilant vapor into close proximity with the article before sterilization can be achieved. Thus, in order to use these methods on articles with long, narrow lumens, it has been necessary to use high concentration of sterilant, extended exposure time, and/or elevated temperatures. For example, lumens longer than 40 cm and/or having an internal diameter of less than 0.4 cm have been particularly difficult to sterilize. Thus, no simple, safe, effective method of sterilizing longer and smaller lumens exists in the prior art.

The sterilization of articles containing diffusion-restricted areas, such as long narrow lumens, presents a special challenge for hydrogen peroxide vapor that has been generated from an aqueous solution of hydrogen peroxide, because: (i) water ($H_2O$) has a higher vapor pressure than hydrogen peroxide ($H_2O_2$), and will vaporize faster than hydrogen peroxide from an aqueous solution; (ii) water has a lower molecular weight than hydrogen peroxide and will diffuse faster than hydrogen peroxide in the vapor state.

Because of this, when an aqueous solution of hydrogen peroxide is vaporized, the innermost locations in a diffusion-restricted lumen will initially see an enhanced $H_2O:H_2O_2$ ratio. This can lead to condensation of water vapor on the surface of the material to be sterilized before sufficient impingement of hydrogen peroxide has reached the innermost locations. The liquid-phase water then becomes a barrier to the penetration of hydrogen peroxide vapor into diffusion restricted areas, such as small crevices and long narrow lumens.

The '145 document cited above discusses the efficacy of highly concentrated hydrogen peroxide for the safe sterilization. The '067984 document discusses the problem of condensed water vapor blocking the diffusion of the sterilant to the bacteria lying on the surface of the material to be sterilized. The Unger document cited above explains the influence of humidity, hydrogen peroxide concentration, and the condensation of the water vapor in detail.

One cannot solve the problem by using more concentrated hydrogen peroxide, since concentrated solutions of hydrogen peroxide, i.e., greater than 60% by weight, can be hazardous, due to the oxidizing nature of the solution. Decomposition of liquid hydrogen peroxide is very exothermic, and releases large volumes of gas, so that stability is a serious concern. Highly-concentrated liquid hydrogen peroxide is so energetic that it has been used as a monopropellant for rocket engines. Moreover, highly concentrated hydrogen peroxide can form unstable reaction products with minor contaminants (such as fingerprint grease), and those reaction products can be a further source of instability.

The above-cited documents '165 (Bier) and '951 (Cummings et al.) both attempt to address this problem. Bier attempts to solve the problem by metering small increments of a hydrogen peroxide solution onto a heated surface to ensure that each increment is vaporized before the next increment is added. This helps to eliminate the difference in the vapor pressure and volatility between hydrogen peroxide and water, but it does not address the fact that water diffuses faster than hydrogen peroxide in the vapor state.

Cummings describes a process for concentrating hydrogen peroxide from a relatively dilute solution of hydrogen peroxide and water and supplying the concentrated hydrogen peroxide in vapor form to a sterilization chamber. The process involves vaporizing a major portion of the water from the solution and removing the water vapor produced before injecting the concentrated hydrogen peroxide vapor into the sterilization chamber as shown in FIG. 1.

FIG. 1 shows the apparatus proposed by Cummings, which includes a vaporizing chamber 7 having any well-known means 3 for injecting into chamber 7 a predetermined amount of a solution of hydrogen peroxide and water. Chamber 7 may be controllably heated by any well-known means. Chamber 7 has an outlet port 2 through which vapors may be exhausted from chamber 7 by means of a vacuum. Port 2 may be opened or closed by valve 11. Chamber 7 also has an outlet port 14 leading through passage 6 to a sterilization chamber 8. Passage 6 may be open or closed by valve 5.

When valve 5 is closed and valve 1 is open; vacuum is applied to chamber 7 to evacuate air. Chamber 7 is heated until the desired temperature within chamber 7 is reached; that temperature is such that, when taken with the pressure within chamber 7, water in the form of vapor will be flashed from a solution of liquid hydrogen peroxide and water present in chamber 7. The process is initiated by the injection into evacuated chamber 7 of predetermined amount of a liquid solution of hydrogen peroxide and water through injection means 3. Conditions within chamber 7 cause the preferential vaporization of water from the solution and the vapor formed thereby is withdrawn from chamber 7 through port 2. At a point in time when a major portion of the water in the injected solution has been vaporized and withdrawn, but before a significant quantity of hydrogen peroxide has vaporized and been withdrawn, valve 1 is closed. What remains in chamber 7 is a hydrogen peroxide-water solution enriched in hydrogen peroxide, specifically greater than 40% hydrogen peroxide by weight, preferably 50 to 80% by weight. Vaporization of this enriched solution continues within chamber 7 and then valve 5 is opened to admit the vapors formed thereby to evacuated sterilization chamber 8. With a substantial amount of the water having been removed, the hydrogen peroxide vapor sterilant is able to disperse itself throughout the sterilizer and penetrate wraps and tubes without encountering a barrier effect that otherwise would have been present by reason of the effects of the present of water discussed above. Thus, the effective concentration of hydrogen peroxide vapor at the point of attack on the goods to be sterilized is markedly enhanced by the process.

Advance Sterilization Products, a division of Johnson and Johnson initially offered Sterrad 100S plasma sterilizer which use 59% wt hydrogen peroxide as sterilant.

Couple of years ago Advance Sterilization Products introduced the more advanced Sterrad 100NX Sterilizer which employs Cummings method of delivering hydrogen peroxide to sterilize devices within the sterilization chamber. In this apparatus a 59% wt aqueous solution of hydrogen peroxide is injected into the delivery system condenser where it is concentrated and then introduced into the chamber. This modified process concentrates the 59% wt hydrogen peroxide to above 80% wt nominal hydrogen peroxide (by selectively vaporizing and removing water) prior to being transferred into the sterilization chamber. Sterrad 100NX range have shorter sterilization cycles and higher lumen sterilization specifications.

The sterilant concentration in the Sterrad 100NX is performed via process similar to Cummings except that the excess vapors is exhausted through the sterilization chamber connected to a vacuum pump instead of outlet 2, FIG. 1. Sterrad's method has a shortcoming that concentration process interrupts the sterilization cycle as it cannot be performed in parallel with the sterilization process.

Further Cummings did not articulate how the hydrogen peroxide concentration process can be controlled accurately.

In the invention disclosed in this application the concentration of the sterilant is performed in parallel with the sterilization process and it is done with sufficient accuracy. This process enables the device to sterilize wide range of sensitive equipment at a shorter sterilization cycle.

BRIEF DESCRIPTION OF THE DRAWINGS

The disclosed inventions will be described with reference to the accompanying drawings, which show important sample embodiments and which are incorporated in the specification hereof by reference, wherein.

DETAILED DESCRIPTION OF SAMPLE EMBODIMENTS

In a hydrogen peroxide vapor plasma sterilizer, the concentration of the hydrogen peroxide sterilant is an important factor in determining sterilization efficacy. This application describes new devices and methods which increase the efficacy of the sterilization cycle in an hydrogen peroxide gas plasma sterilization system by increasing and controlling the concentration of the liquid sterilant within the device, without requiring any handling or transportation of highly concentrated sterilant.

The present application use a novel injector-concentrator arrangement. This arrangement provides accurate control of concentration of the liquid-phase hydrogen peroxide, prior to vaporization of the liquid sterilant for release into the sterilization chamber. This increases the efficacy of the sterilization cycle.

The numerous innovative teachings of the present application will be described with particular reference to presently preferred embodiments (by way of example, and not of limitation). The present application describes several inventions, and none of the statements below should be taken as limiting the claims generally.

The hydrogen peroxide gas plasma sterilization cycle is well understood and documented.

Figure 1:
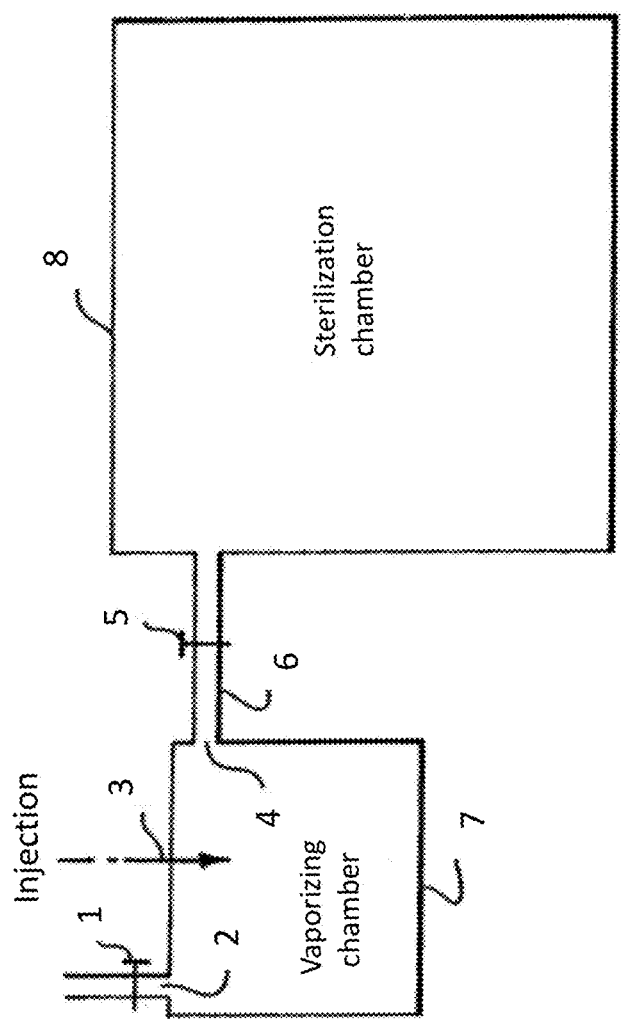
FIG. 1 shows a previously proposed apparatus to concentrating a liquid hydrogen peroxide solution.
Figure 2:
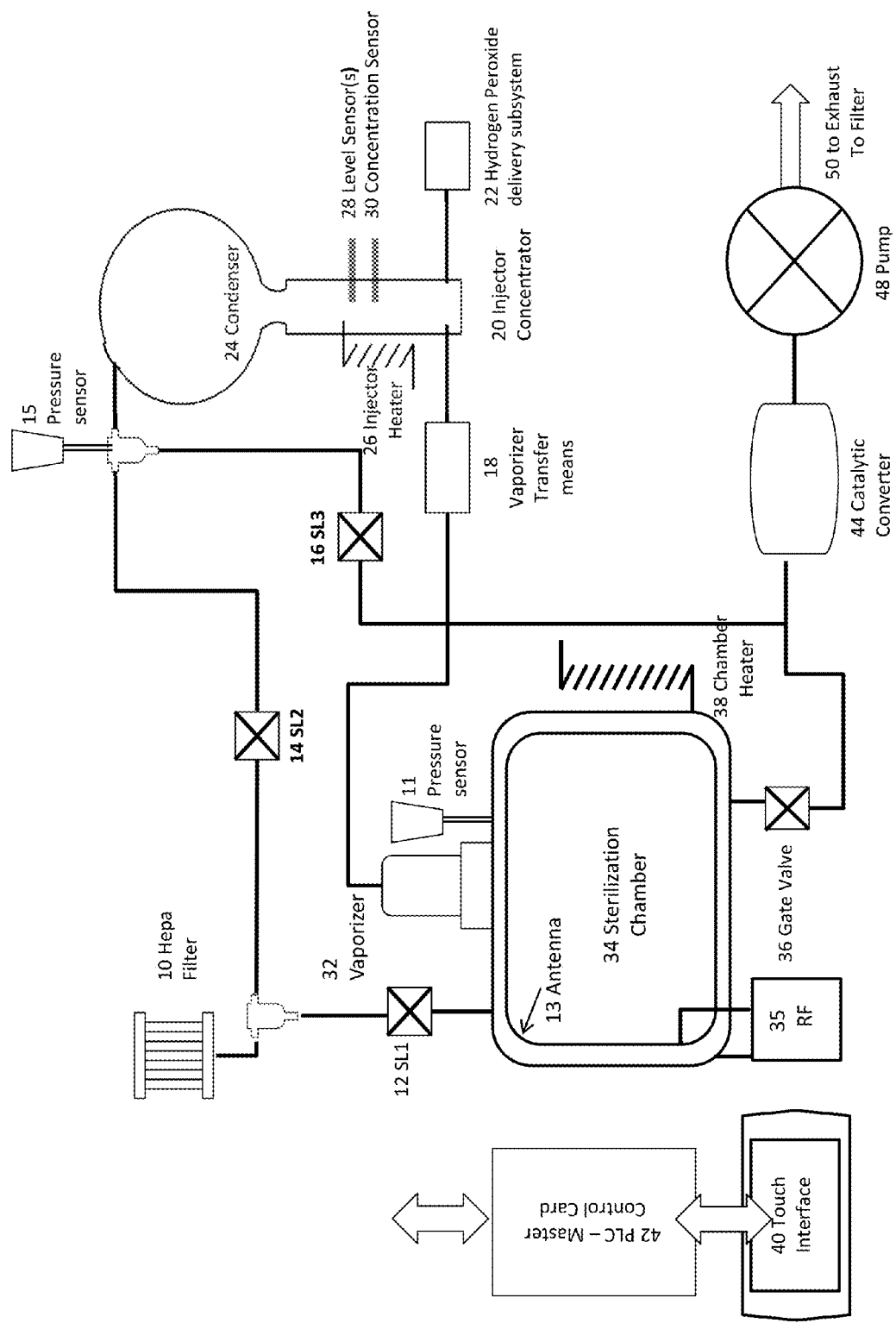
FIG. 2 shows the schematic of preferred embodiment of the hydrogen peroxide injector concentrator as deployed in a typical sterilizer configuration.
Figure 3:
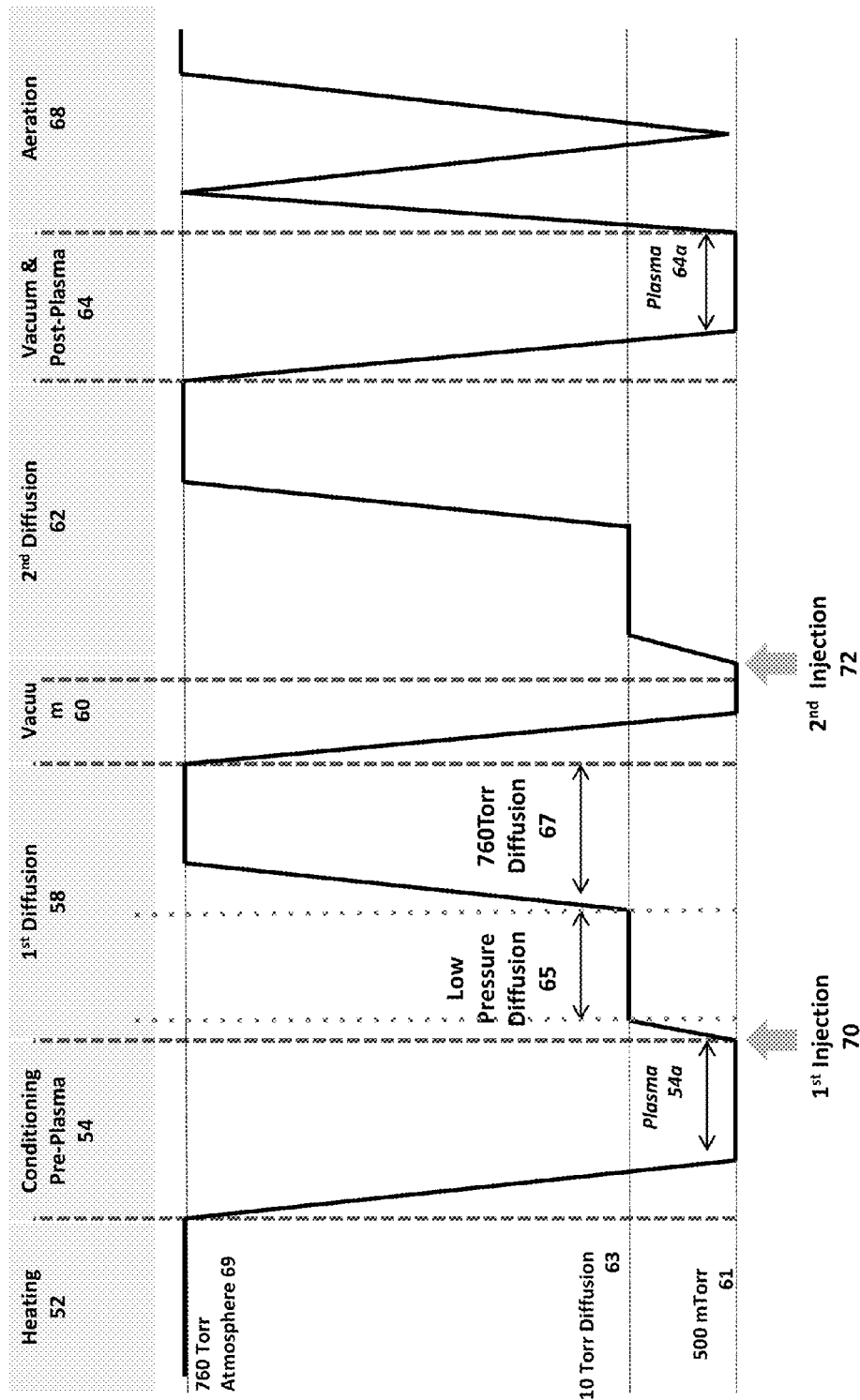
FIG. 3 shows pressure curve within the sterilization chamber during a typical full hydrogen peroxide gas plasma sterilization cycle.

FIG. 2 shows the schematic of preferred embodiment of the hydrogen peroxide injector—concentrator as deployed in a typical sterilizer, and FIG. 3 shows the state of the sterilization chamber during a typical sterilization cycle. In a typical cycle the washed and dried medical instruments to be sterilized are packed into sealed tyvek pouches and placed into the heated sterilization chamber 34 of the sterilizer. During the heating process 52 the temperature within the chamber is increased to around 48-55 degree centigrade. Depending on the power consumption of the heating resistance 38, this process can take e.g. 10-15 minutes.

The chamber pressure is then reduced to a sufficiently low to start a plasma within the chamber by an RF generator attached to antenna 13 and the chamber 34. Preferable the chamber pressure should be below 500 mT during this plasma pre-conditioning phase 54. The chamber pressure is monitored via a pressure gauge 11. The plasma generated within the chamber generates and homogenously distributes heat within the chamber and further ensures evaporation of any residual water from the medical instruments.

After pre-conditioning liquid hydrogen plasma is injected (70) into a pre-heated vaporizer 32 intermittently in small volumes say in 6-20 pulses with 8-15 sec duration between the pulses. The benefits of the pulsed injection is described in the Cummings' US patent. In the vaporizer the sterilant is converted into vapor which is then released to the sterilization chamber.

With the injection the chamber pressure rises approximately to 10-15 Torr pressure. The chamber pressure remains at this level for a period of low pressure diffusion 65. Typically this process lasts about for approximately 4-8 minutes. During this period hydrogen peroxide vapor is expected to diffuse homogenously inside the chamber and into the medical instruments in the $H_2O_2$ permeable pouches. During the $1^{st}$ and second diffusion (58 and 62 respectively) the sterilization chamber temperature and pressure are the critical parameters effecting the sterilization cycle efficacy and controlled by well known means and in a well known process.

Following the low diffusion, conditioned air is introduced into the chamber through a HEPA filter 10 into the chamber via electrically controlled solenoids SL1 (12) and the chamber pressure is raised up to atmospheric pressure 69 for the 760 Torr diffusion period 67 for about 2-15 minutes depending on the particular sterilization program selected for a given lumen length and material of a medical instrument to be sterilized. A short duration may not be sufficient for hydrogen peroxide molecules to penetrate a narrow and long lumen despite the increased pressure. The optimum diffusion duration for a given lumen and for a device is established empirically by exhaustive tests carried out by following the half cycle validation guidelines provided by ISO 14937 standards.

This cycle then repeated for further sterilization assurance (see FIG. 3), e.g. vacuuming 60, followed by 2nd injection 72 and 2nd diffusion 62. This phase is followed by evacuation to low vacuum 64 and application of RF energy to generate plasma. The plasma ensures hydrogen peroxide molecules left in the chamber and on the pouches to be decomposed into free radicals and eventually water and oxygen. The free radicals thus generated together with the UV radiated from the plasma further improve the sterilization efficacy.

At the final aeration phase 68 ventilates the chamber and further ensures that the medical equipment to be sterilized is cleaned from any residual excess hydrogen peroxide. During the evacuation any remaining hydrogen peroxide molecules that survived the plasma and left the chamber are trapped within the catalytic converter 44 before extracted by the pump 48 and exhausted via a filter 50.

In the preferred embodiment described above SL1 (12), SL2 (14), SL3 (16) are two way valves used to prevent or admit the flow of liquid, vapor and filtered and dehumidified air controlled by dedicated computer, the master controller card 42 which receives input commands via touch sensitive screen graphical user interface 40. The solenoid which expose to liquid or vapour sterilant should be made from materials that are chemically resistive to hydrogen peroxide transmission.

In the plasma sterilizer depicted in FIG. 2, the hydrogen peroxide delivery sub-system 22 delivers a low concentration sterilant liquid from a small container or cartridge to the injector concentrator 20. The concentration of the sterilant within the container or cartridges are kept below 60% due to transport restriction. The delivery process is a well know art and usually involves filling up the injector until a level sensor 28 provides a signal to the master controller 42.

In one embodiment the level detection within the injector is performed by placing two stainless steel metal pins opposing to each other to measure resistivity of the medium. If both pins are in hydrogen peroxide liquid then it would present a corresponding circuit a lower resistance.

In one embodiment, if there is an overfill then the solenoid SL2 (73) and solenoid SL3 (75) could be used to make further fine adjustments. For this purpose the SL3 could provides low vacuum suction option as it is connected to the evacuating pump 49 via catalytic converter 44 whereas the SL2 provides atmospheric pressure. By controlling these solenoids in harmony with two way hydrogen peroxide delivery system 89 it is possible to adjust the liquid level via relatively simple and well understood art.

In the disclosed inventions, the concentration of the hydrogen peroxide is a critical parameter. The disclosed injector concentrator (shown separately in FIG. 4A) is used to control this critical parameter. Within this unit the sterilants concentration is increased in a controlled manner up to a pre-determined level say above 80% wt or above 90% weight.

During the concentration process the injector concentrator is kept heated in a standby mode via injector heater 93. Once a fixed amount of sterilant (say 5.2 ml for a sterilizer with a 110 liter sterlization chamber) has filled into the injector, then the pressure of the concentrator is reduced by intermittently opening and closing SL3 (75). Concurrently the injector heater 93 power is increased to force the liquid sterilant to boil. By controlling the condenser pressure via monitoring the pressure sensor (95) and power input to the heater 93 it is possible to create conditions where major portion of the water within the sterilant is vaporized which is suctioned out via the suction solenoid SL3 (75) intermittently. The condenser is kept at the ambient temperature or kept at a lower temperature than the injector with heater in order to create a temperature gradient encouraging any escaping hydrogen peroxide to condense and return back to the injector while due to low pressure, water continues to remain in vapor phase.

Figure 5:
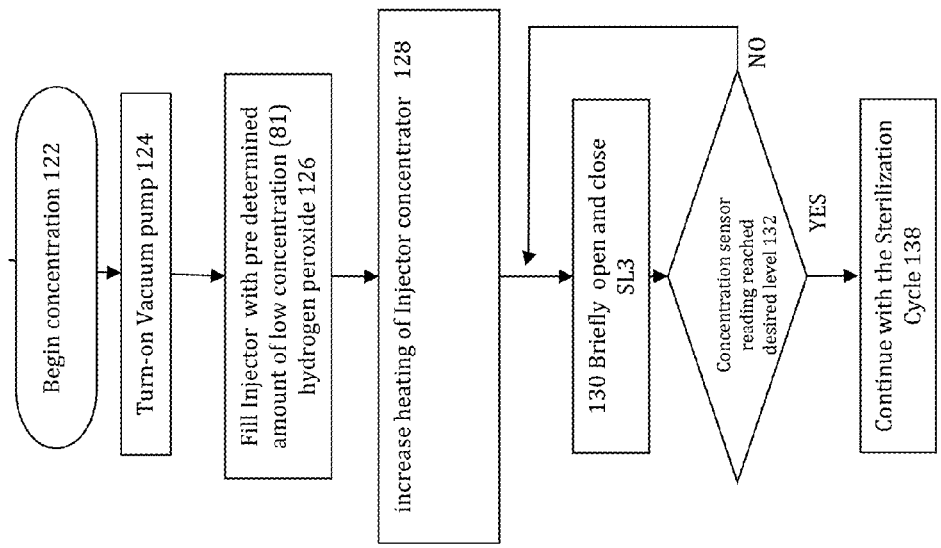
FIG. 5 shows a flow chart of concentration of the injector-concentrator

During concentration process the concentration level is continuously monitored by measuring the electrical resistance of the hydrogen peroxide via sensors placed in the injector. FIG. 5 depicts the flow chart of the preferred concentration process.

Typically during the standby state of the sterilizer the sterilization chamber, vaporizer, catalytic converter and Injector concentrator are kept heated at predetermined levels. All solenoids SL1, SL2 and SL3 are s are closed and the pump is turned off The sterilization process usually starts after the medical instruments are loaded into the sterilization chamber and the door is securely locked via a command on the touch screen attached to the device. Once the sterilization cycle is started the vacuum pump is turned on and subsequently the hydrogen peroxide delivery subsystem delivers pre-determined amount of low concentration hydrogen peroxide liquid into the injector concentrator. The amount delivered depends on whether concentrated or non concentrated cycle is selected. The injector heater power is increased from its standby level and the solenoid SL3 (16) is briefly opened and closed intermittently (said brief period which can be determined empirically) to lower the pressure of the condenser and cause the sterilant to boil 128 FIG. 5. Once the critical low pressure and high temperature is reached the hydrogen peroxide within the injector boils and preferentially water vapor is extracted from the condenser chamber. At this stage it would be beneficial to monitor the condenser pressure via a pressure sensor 11 FIG. 2.

During concentration the solenoid SL3 (16) is opened and closed intermittently to extract vapor wherein said brief period which can be determined empirically. Following this the concentration level sensor reading is taken to examine whether the desired concentration level is reached 132.

The position of the concentration level sensor pins can be determined empirically via repeated experiments involving sampling the sterilant during concentration at recorded levels and measuring the density of the sampled sterilant while keeping the concentration process parameters unchanged. Usually hydrogen peroxide concentration within the chamber is expected to be around 15-20 mg/L which determines the target sterilant volume which will be injected into the chamber for a given concentration level.

In another embodiment the electrical resistance characteristics of the hydrogen peroxide is continuously and accurately monitored and upon reaching a preset resistance level corresponding to 82% wt or 92% wt the concentration is terminated.

Once the desired concentration level of the sterilant is reached then the liquid sterilant is transferred intermittently into the vaporizer 134 and the diffusion cycle of the sterilization starts 138.

The hydrogen peroxide sterilant is usually available with various amounts of stabilizers (phosphate derivatives etc.) which can vary its electrical resistance characteristics and the rate of its electrical resistance varies with concentration. In the preferred embodiment the electrical characteristics of the particular sterilant used is drawn as a plot against the concentration level. The concentration of the $H_2O_2$ can be measured independently via a densitometer or any other well known means.

In another embodiment the electrical resistance characteristics of the hydrogen peroxide is continuously monitored and upon reaching a desired level around 87-92% wt the concentration is terminated.

In another embodiment the concentration process is terminated when a predetermined volume or weight of sterilant remains in the injector. For this aim the boiling process in the injector can be stopped and the volume of the hydrogen peroxide is measured via electrical level sensors or weight sensors or optically or by capacitive measurements or other well known means. This predetermined volume can be established empirically via repeated experiments involving measuring the density of the remaining liquid sterilant versus the volume and weight (or both) of the remaining sterilant while keeping the concentration process parameters unchanged.

In another embodiment the concentration process is terminated after a fixed duration. This fixed duration can be established empirically by repeated experiments to extract typical durations required to reached desired concentrations for a give concentrator temperature and condenser pressure range.

Figures 4A, 4B:
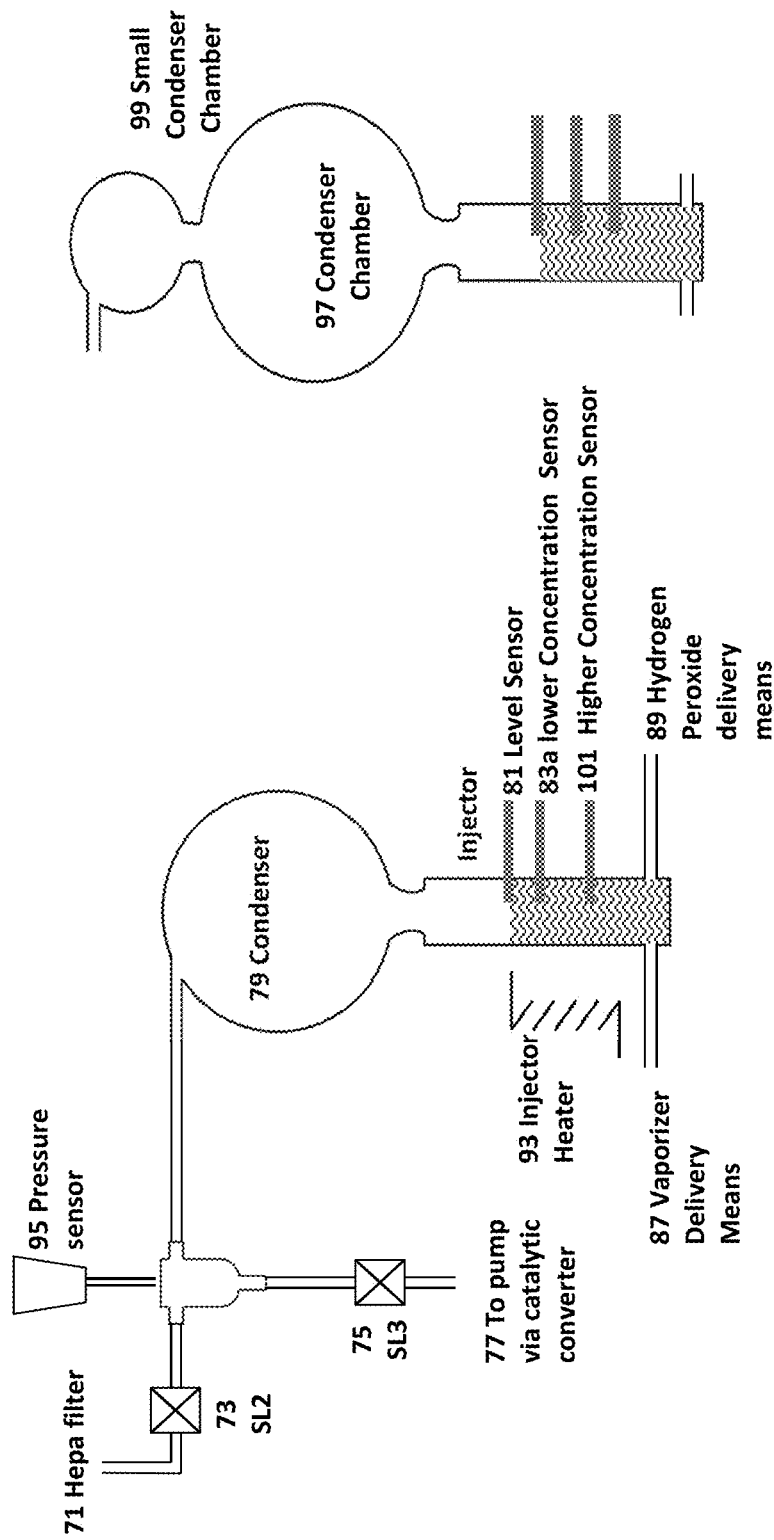
FIG. 4A shows an injector-concentrator embodiment.
FIG. 4B shows an alternative injector-concentrator embodiment.

FIG. 4B shows the schematic of another embodiment of the injector concentrator wherein the main condenser chamber 97 is complemented by a secondary small condenser chamber 99 which may results better condensation efficiency. The liquid concentration is a well known art and the shape and material of the injector concentrator can be designed to further improve the concentration efficiency and hence reduce the duration of the process.

Figure 6:
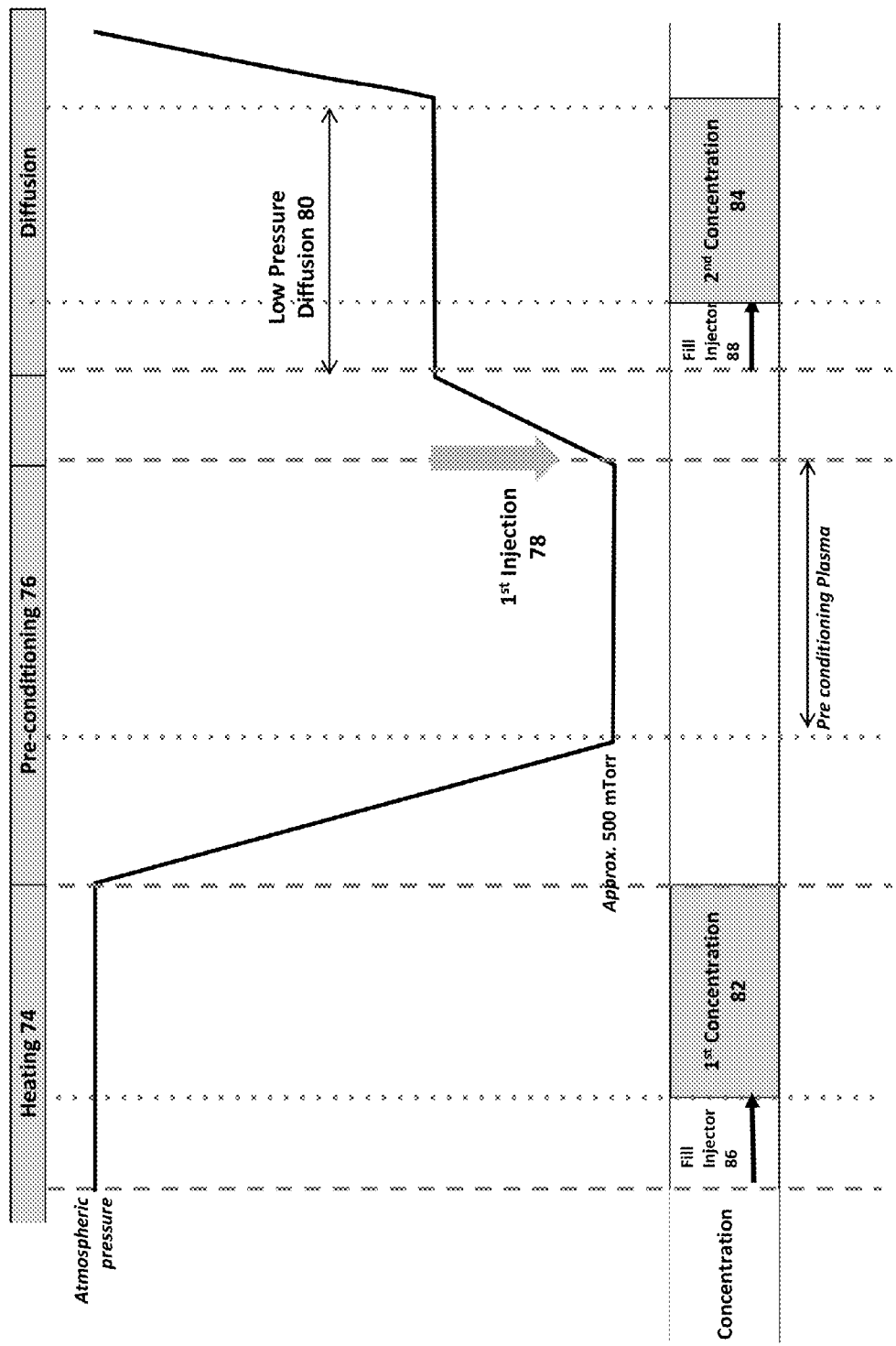
FIG. 6 schematically shows integration of a separate hydrogen peroxide concentration into a typical hydrogen peroxide gas plasma sterilization cycle.

As presented earlier in a plasma sterilizer the sterilization cycle is repeated twice for sterilization assurance. In the example of FIG. 6, the concentration process 82 for the first injection 78 is carried out during heating of the sterilization chamber 74. During the heating the gate valve 36 is closed 92 the pump 48 is turned on 90 and the injector is filled 86 and the concentration process 82 begins. In the preferred embodiment the second concentration for the second cycle is performed during the low pressure low pressure 1st diffusion 80 which typically lasts 8 minutes and provides sufficient time for the concentration process.

In another embodiment it is possible to concentrate the sterilant at double volume which would be sufficient for two injections. In this case the injector concentrator would be designed to hold double amount of sterilant and Vaporizer delivery means 18 only delivers the half of the volume of the concentrated sterilant at each injection.

Figure 7:
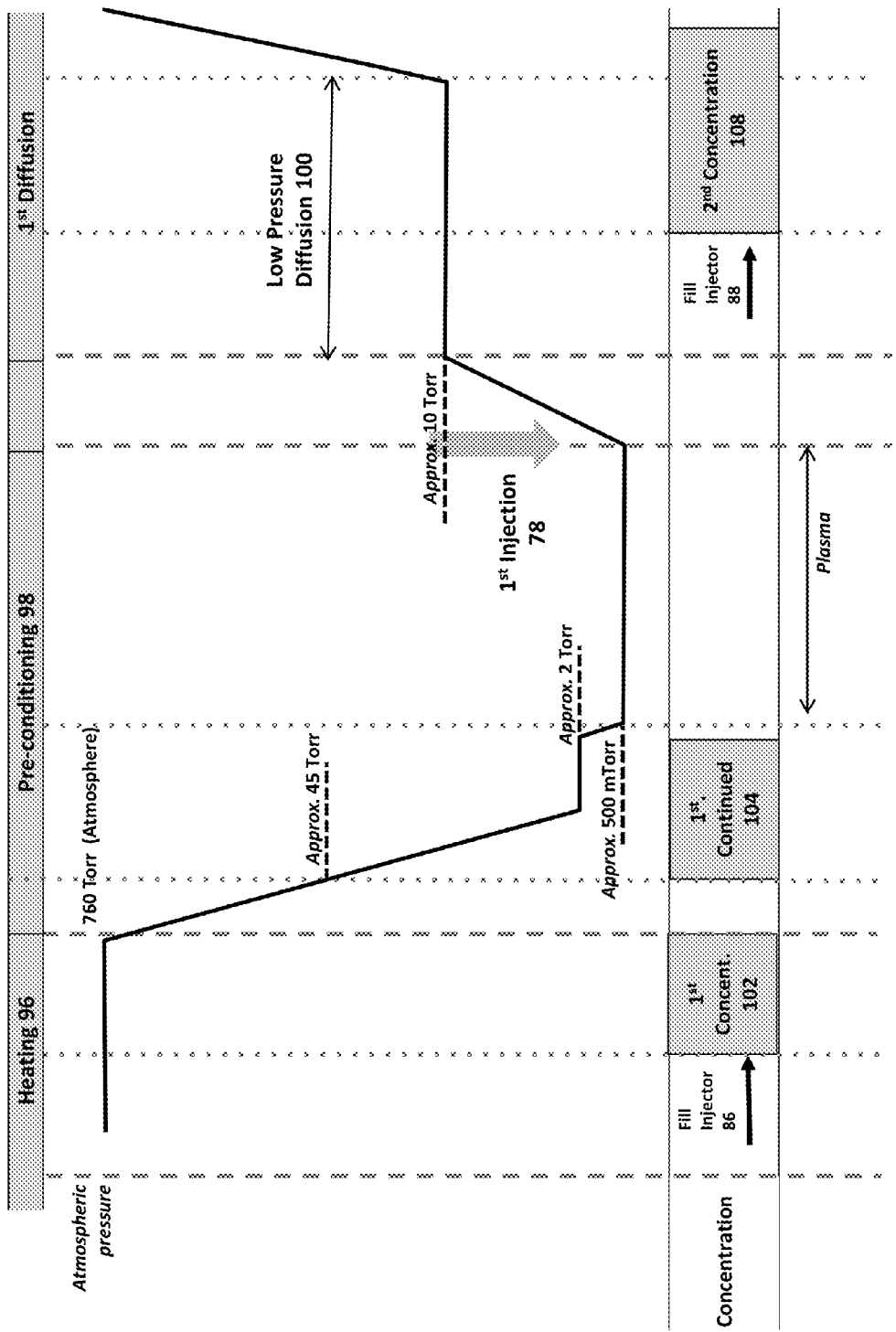
FIG. 7 shows an alternative integration of the hydrogen peroxide concentration into a typical hydrogen peroxide gas plasma sterilization cycle.

FIG. 7 shows an alternative integration of the hydrogen peroxide concentration process into the first sterilization cycle. In this embodiment in order to further reduce the sterilization cycle duration, the concentration process is performed partially during the heating 96 and partially during a portion of the pre-conditioning 98. Because there is only one pump employed which is used for both evacuating the air from the chamber 44 as well as the condenser 24, once the gate valve 36 is opened then the solenoid SL3 becomes ineffective. In this embodiment the concentration process can resume 104 when the chamber pressure drops down to say 45 Tor. During the concentration 104 it may not be possible to bring the chamber pressure low enough for the plasma to trigger since the gate vane is open and the water vapor is suctioned from the condenser. However once the concentration is finished the chamber pressure can be brought down to say 500 mT and the plasma starts. In another embodiment all of the concentration is done fully during the pre-conditioning plasma 54a FIG. 3 after closing the gave vane 36.

Further in the preferred embodiment it is possible to start continue the 2nd concentration 108 even after raising the chamber pressure to the atmospheric level for the high diffusion as depicted in FIG. 6. This scheme offers a solution if the low pressure diffusion duration 107 is too short to accommodate the second concentration 108.

In another embodiment the evacuation of the condenser chamber of the injector concentrator is done by employing a separate pump other than the pump used to evacuate the sterilization chamber. This would allow greater flexibility in deciding the start time of the concentration process. The evacuated vapor does still need through the catalytic converter to trap any hydrogen peroxide which escapes the condenser.

The preferred embodiment has been implemented and tested in Stericool 110S model from GOA Technologies. It has been validated that consistently high concentration level achieved (85-90%) contributed significantly to the sterilization efficacy of the device particularly when used with long lumens. The extent of penetration of hydrogen peroxide into a tube is measured by colorimetrically assaying the amount of hydrogen peroxide deposited on the special purpose hydrogen peroxide chemical indicators placed in standard lumen set.

In order to support sterilization of certain type of medical equipment which may be sensitive to highly concentrator hydrogen peroxide vapor it may be desirable to introduce a special sterilization program for these devices where the concentration level may be set to a lower concentration level say 70% by weight via the means described herein or keep it unchanged. In the disclosed invention the injector concentrator design can be modified to support dual action of concentrated process or non concentrated process or multiple level of concentration on the same device. This means wide range of medical equipment including those sensitive to concentrated hydrogen peroxide vapor can be sterilized within the same equipment by simply adapting an appropriate sterilization program.

When a non-concentrated program is selected the sterilization cycle process will follow the steps described in paragraphs 0005 to 00012 above. For the non-concentrated program the amount of hydrogen peroxide vapor released into the sterilization chamber will be different than the amount released via concentrated program cycle. This requirement can be met by introducing an additional none-concentrated program level sensor which could be used to limit the sterilant volume allowed into the injector to be at this preset level. In the disclosed embodiment when the non-concentrated program is selected the controlling computer program uses the reading on this secondary level sensor and limits the hydrogen peroxide volume to this level as described in the steps above. The actual amount of hydrogen peroxide used for the non concentrated process would be around 0.04 to 0.06 ml H2O2 per liter of the sterilization chamber volume. Alternatively if a concentrator program is selected than the computer program reads the sensor 101 in FIG. 7.

In another embodiment the non-concentrated program may have different diffusion time and temperature and chamber pressure parameters than the concentrated program. Each of these parameters can be experimentally optimized. Once this optimization is completed than exhaustive tests must be carried out by following the half cycle validation guidelines provided by ISO 14937 standards to validate the each process.

Further in order to assess any damage to the sensitive medical equipment it would be necessary to expose said equipment to repeated sterilization cycles and study the aging under microscope or using other appropriate tools.

The disclosed innovations, in various embodiments, provide one or more of at least the following advantages. However, not all of these advantages result from every one of the innovations disclosed, and this list of advantages does not limit the various claimed inventions.

Sterilization of wide range of sensitive medical instruments
Faster throughput;
Better than $10^{-6}$ sterilization;
Shorter cycle time;
Better safety;
Lower cost of consumables;
Better results with articles having long thin lumens;
Faster process with articles having long thin lumens;
Reduced likelihood of handling toxic exhaust and/or byproduct;
Fewer uncontrolled process variables; and/or
Fewer safety concerns.

According to some but not necessarily all embodiments, there is provided: A process for introducing concentrated hydrogen peroxide vapor to interior surfaces of medical instruments with lumens in an evacuated sterilization chamber comprising the steps of: filling an injector concentrator at a predetermined volume of liquid solution of relatively dilute hydrogen peroxide; heating the injector concentrator and evacuating its condenser chamber to preferentially vaporize the water content of the said liquid into a condenser prior to vacuuming said sterilization chamber; intermittently withdrawing a portion of said water vapor from said condenser chamber via vacuum suction to concentrate said hydrogen peroxide remaining in said injector concentrator; terminating said withdrawal of water vapor from said condenser chamber when said remaining hydrogen peroxide is measured to be sufficiently concentrated so as to produce, concentrated hydrogen peroxide greater than about 80% by weight; intermittently transferring the said concentrated hydrogen peroxide liquid in small volumes into a separate pre heated vaporizer connected to the sterilization chamber; and maintaining said hydrogen peroxide vapors in contact with said medical instruments until sterilization is achieved.

According to some but not necessarily all embodiments, there is provided: A sterilization process, comprising the steps, in any order unless specifically stated, of: placing objects to be sterilized into a sterilization chamber; performing a low-pressure evaporation procedure on an initial volume of aqueous hydrogen peroxide which has an initial concentration of less than about 60% wt hydrogen peroxide, to extract water vapor therefrom, without passing the water vapor through the sterilization chamber, until the resulting concentrated hydrogen peroxide is measured to have reached at least a target concentration value; said target concentration value being greater than 80% wt; evacuating said sterilization chamber, and generating a plasma in a space which is continuous with said sterilization chamber for a period; and then vaporizing at least some of the concentrated hydrogen peroxide into said sterilization chamber; holding said sterilization chamber at a pressure of less than 50 Torr for more than 3 minutes, while said concentrated hydrogen peroxide remains present in the vapor phase; and then rapidly increasing the pressure of said sterilization chamber, whereby a net flow of concentrated hydrogen peroxide vapor into the interior of lumens of said objects occurs; wherein said concentrating and vaporizing steps are performed at different locations within a single machine.

According to some but not necessarily all embodiments, there is provided: A sterilization process, comprising the steps, in any order, of: placing objects to be sterilized into a sterilization chamber; performing a low-pressure evaporation procedure on an initial volume of aqueous hydrogen peroxide to extract water vapor therefrom until the resulting concentrated hydrogen peroxide is known to have reached at least a target concentration value; said target concentration value being greater than 80% wt; evacuating said sterilization chamber; transferring at least some of said concentrated hydrogen peroxide into a vaporizer, and vaporizing at least some of the concentrated hydrogen peroxide from said vaporizer into said sterilization chamber; and holding said sterilization chamber at a pressure of less than 50 Torr for more than 3 minutes, while said concentrated hydrogen peroxide remains present in the vapor phase; wherein said concentrating and vaporizing steps are performed within a single machine.

According to some but not necessarily all embodiments, there is provided: A sterilization process, comprising the steps, in any order, of: placing objects to be sterilized into a sterilization chamber; concentrating aqueous hydrogen peroxide until the resulting concentrated hydrogen peroxide is known to have reached at least a target concentration value; said target concentration value being greater than 80% wt; evacuating said sterilization chamber, and vaporizing at least some of the concentrated hydrogen peroxide into said sterilization chamber at less than 50 Torr for a duration and then rapidly increasing the pressure of said sterilization chamber, whereby a net flow of concentrated hydrogen peroxide vapor into the interior of lumens of said objects occurs; wherein said concentrating and vaporizing steps are performed by different parts of a single machine According to some but not necessarily all embodiments, there is provided: A sterilization process, comprising the steps, in any order, of: placing objects to be sterilized into a sterilization chamber; concentrating aqueous hydrogen peroxide until the resulting concentrated hydrogen peroxide is known to have reached at least a target concentration value; said target concentration value being greater than 80% wt; evacuating said sterilization chamber, generating a plasma within said chamber for a determined duration, and then vaporizing at least some of the concentrated hydrogen peroxide into said sterilization chamber; and holding a concentrated hydrogen peroxide vapor in said chamber, for long enough to reduce the population bacteria therein by at least a factor of a million; wherein said concentrating and vaporizing steps are performed within a single machine According to some but not necessarily all embodiments, there is provided: A sterilization system, comprising, in a single unit: a sterilization chamber; a concentrator which performs a low-pressure evaporation procedure on an initial volume of aqueous hydrogen peroxide, to extract water vapor therefrom until the resulting concentrated hydrogen peroxide is known to have reached at least a target concentration value; said target concentration value being greater than 80% wt; a vaporizer, which vaporizes at least some of the concentrated hydrogen peroxide into said sterilization chamber; and a valve from said chamber to a vacuum manifold, and another valve from said concentrator to said vacuum manifold; wherein said concentrating and vaporizing steps are performed within a single machine.

According to some but not necessarily all embodiments, there is provided: sterilizers, and sterilization methods, which use a novel injector-concentrator arrangement. This arrangement provides accurate control of concentration of the liquid-phase hydrogen peroxide, prior to vaporization of the liquid sterilant into the sterilization chamber. This increases the reliability and efficacy of the sterilization cycle.

According to some but not necessarily all embodiments, there is provided: A process for introducing concentrated hydrogen peroxide vapor to interior surfaces of medical instruments with lumens in an evacuated sterilization chamber comprising the steps of selecting concentrated or non-concentrated sterilization program manually on the user interface screen (40 FIG. 2) appropriate to the medical device that will be sterilized; then if a concentrated program is selected; filling an injector concentrator at a predetermined volume of liquid solution of relatively dilute hydrogen peroxide; heating the injector concentrator and evacuating its condenser chamber to preferentially vaporize the water content of the said liquid into a condenser prior to vacuuming said sterilization chamber; intermittently withdrawing a portion of said water vapor from said condenser chamber via vacuum suction to concentrate said hydrogen peroxide remaining in said injector concentrator; terminating said withdrawal of water vapor from said condenser chamber when said remaining hydrogen peroxide is measured to be sufficiently concentrated so as to produce, concentrated hydrogen peroxide greater than about 80% by weight via a help of a lower concentration sensor or to produce, concentrated hydrogen peroxide greater than about 90% by weight via a help of a higher concentration sensor; alternatively if the non-concentrated program is selected simply filling an injector concentrator at a different predetermined volume of liquid solution of relatively dilute hydrogen peroxide via a help of a non concentration level sensor; then for both concentrated and non-concentrated programs doing the executing the following steps; intermittently transferring the said concentrated hydrogen peroxide liquid in small volumes into a separate pre heated vaporizer connected to the sterilization chamber; and maintaining said hydrogen peroxide vapors in contact with said medical instruments until sterilization is achieved.

There are currently available hydrogen peroxide vapor sterilizers which do not employ plasma in the sterilization chamber. Therefore in these systems there are no corresponding plasma phase (54*a* and 64*a*, FIG. 3). In these systems the sterilant vapour exhausted from the chamber and decomposed within either a catalytic converter or a separate small plasma chamber. The sterilant concentration process described herein can easily be integrated into these sterilizers by concentration the sterilant prior to the vacuuming of the sterilization chamber as described 82 FIG. 6 and or during the diffusion cycle 58 FIG. 6.

In another embodiment the non-concentrated program may have a higher diffusion pressure and or lower chamber temperature. These parameters can be experimentally optimized to reduce the chemical aggressiveness of the sterilant in its vaporized form on specific sensitive medical equipment and materials. Once such an optimization is completed than exhaustive tests must be carried out by following the half cycle validation guidelines provided by ISO 14937 standards to validate the each process with new parameters.

Modifications and Variations

As will be recognized by those skilled in the art, the innovative concepts described in the present application can be modified and varied over a tremendous range of applications, and accordingly the scope of patented subject matter is not limited by any of the specific exemplary teachings given. It is intended to embrace all such alternatives, modifications and variations that fall within the spirit and broad scope of the appended claims.

None of the description in the present application should be read as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 USC section 112 unless the exact words "means for" are followed by a participle.

The claims as filed are intended to be as comprehensive as possible, and NO subject matter is intentionally relinquished, dedicated, or abandoned.

What is claimed is:

1. A method for introducing hydrogen peroxide vapor at different concentration levels to interior surfaces of lumens of medical instruments inside a sterilization chamber of a single sterilizer, comprising the steps of:

obtaining a user input via a user interface of said single sterilizer;

selecting one of a plurality of sterilization programs using said user input, wherein the plurality of sterilization programs includes a non-concentrated sterilization program and at least one concentrated sterilization program;

partially filling an injector concentrator of said single sterilizer with an initial volume of liquid hydrogen peroxide solution, wherein said initial volume is determined by said selected sterilization program, wherein said liquid hydrogen peroxide solution has an initial concentration of less than 60% by weight;

when said selected sterilization program is a concentrated sterilization program, preferentially vaporizing the water content of said liquid hydrogen peroxide solution by heating said injector concentrator and intermittently evacuating a condenser chamber connected to said injector concentrator using a vacuum pump, wherein said intermittent evacuation removes a portion of any vaporized water content in said condenser chamber, and wherein said vacuum pump can independently evacuate said condenser chamber regardless of the pressure within said sterilization chamber; and terminating said preferential vaporizing when the remaining liquid hydrogen peroxide solution in said injector concentrator is measured to exceed a target concentration, wherein said target concentration is determined by said selected sterilization program;

then for all sterilization programs, intermittently transferring a portion of the liquid hydrogen peroxide solution from said injector concentrator to a separate pre-heated vaporizer of said single sterilizer, wherein said vaporizer is connected to both said injector concentrator and to said sterilization chamber;

vaporizing any liquid hydrogen peroxide solution in said vaporizer into hydrogen peroxide vapor; and maintaining said hydrogen peroxide vapor in contact with said medical instruments as part of a diffusion cycle until sterilization is achieved.

2. The method of claim 1, further comprising generating a plasma in said sterilization chamber using an RF generator, wherein said plasma generation occurs prior to said diffusion cycle.

3. The method of claim 2, wherein said plasma generation occurs at least partially contemporaneously to said partial filling and/or preferential vaporizing.

4. The method of claim 1, wherein said target concentration is greater than 90% by weight and less than 95% by weight.

5. The method of claim 1, wherein when said selected sterilization program is a non-concentrated sterilization program then filling the injector concentrator to a separate predetermined level and continuing the non-concentrated sterilization program.

6. The method of claim 1, wherein level sensing on the injector concentrator is performed by a capacitive level sensor.

* * * * *